United States Patent [19]

Freeburne et al.

[11] Patent Number: 5,629,438

[45] Date of Patent: May 13, 1997

[54] HYDROCHLORINATION PROCESS FOR CONVERTING HIGH-BOILING RESIDUE FROM DIRECT PROCESS TO MONOSILANES

[75] Inventors: Steven K. Freeburne, Edgewood; Robert F. Jarvis, Jr., Union, both of Ky.

[73] Assignee: Dow Corning Corporation, Midland, Mich.

[21] Appl. No.: 712,226

[22] Filed: Sep. 11, 1996

[51] Int. Cl.$^6$ .................................................. C07F 7/08
[52] U.S. Cl. ..................... 556/466; 556/467; 556/468
[58] Field of Search ..................... 556/466, 467, 556/468

[56] References Cited

U.S. PATENT DOCUMENTS

| | | |
|---|---|---|
| 2,380,995 | 8/1945 | Rochow . |
| 2,488,487 | 11/1949 | Barry et al. . |
| 2,598,435 | 5/1952 | Mohler et al. . |
| 2,681,355 | 6/1954 | Barry et al. . |
| 2,709,176 | 5/1955 | Bluestein . |
| 4,393,229 | 7/1983 | Ritzer et al. . |
| 5,175,329 | 12/1992 | Bokerman et al. . |
| 5,292,912 | 3/1994 | Chadwick . |
| 5,321,147 | 6/1994 | Chadwick et al. ............ 556/466 |
| 5,326,896 | 7/1994 | Chadwick et al. ............ 556/466 |
| 5,430,168 | 7/1995 | Ferguson et al. . |

*Primary Examiner*—Paul F. Shaver
*Attorney, Agent, or Firm*—William F. Boley

[57] ABSTRACT

A hydrochlorination process for the production of monosilanes from the high-boiling residue resulting from the reaction of organochlorides with silicon metalloid in a process typically referred to as the "direct process." The process comprises (A) forming a mixture comprising the high-boiling residue and an organosilane and (B) contacting the mixture with hydrogen chloride in the presence of a catalytic amount of a catalyst composition effective in promoting the formation of monosilanes from the high-boiling residue. A preferred catalyst composition comprises aluminum trichloride, at least a portion of which may be formed in situ during conduct of the direct process and isolation of the high-boiling residue.

19 Claims, No Drawings

HYDROCHLORINATION PROCESS FOR CONVERTING HIGH-BOILING RESIDUE FROM DIRECT PROCESS TO MONOSILANES

BACKGROUND OF INVENTION

The present invention is a hydrochlorination process for the production of monosilanes from the high-boiling residue resulting from the reaction of organochlorides with silicon metalloid in a process typically referred to as the "direct process." The process comprises forming a mixture comprising the high-boiling residue and an organosilane and contacting the mixture with hydrogen chloride in the presence of a catalytic amount of a catalyst composition effective in promoting the formation of monosilanes from the high-boiling residue. A preferred catalyst composition for use in the present process comprises aluminum trichloride, at least a portion of which may be formed in situ during conduct of the direct process and isolation of the high-boiling residue.

In the preparation of organochlorosilanes by the direct process a complex mixture is formed which is typically distilled to separate monosilanes from other components present in the mixture. For example, in the "direct process," in addition to the monosilanes which in the case of the chloromonosilanes include dimethyldichlorosilane, methyltrichlorosilane, and trimethylchlorosilane there is obtained a residue which boils above the organochlorosilanes, that is above about 70° C. This residue is hereinafter referred to as "high-boiling residue."

The "direct process" is well described in she patent literature, for example, in Rochow, U.S. Pat. No. 2,380,995, issued Aug. 7, 1945, and Barry et al., U.S. Pat. No. 2,488,487, issued Nov. 15, 1949. The residue remaining after distillation overhead of the monosilanes is a complex mixture comprising higher boiling silicon containing compounds which have, for example, SiSi, SiOSi, and SiCSi linkages in the molecules. The residue may also contain silicon particulates and metals or compounds thereof. Typical high-boiling residues obtained from distillation of product from the direct process are described, for example, in Mohler et al., U.S. Pat. No. 2,598,435, issued May 27, 1952, and Barry et al., U.S. Pat. No. 2,681,355, issued Jun. 15, 1954.

In current commercial operations for performing the direct process, the high-boiling residue can constitute as much as five weight percent of the resultant product. Therefore, it is desirable to convert the high-boiling residue into commercially desirable products to both reduce waste disposal and to improve raw material utilization.

Ritzer et al., U.S. Pat. No. 4,393,229, describe a process for converting alkyl-rich disilanes in a residue obtained from the manufacture of alkylhalosilanes to halogen-rich polysilanes. The process comprises treating an alkyl-rich disilane-containing residue with an alkyltrihalosilane or silicon tetrahalide in the presence of a catalyst and a catalytic amount of a hydrosilane reaction promoter at an elevated temperature. Ritzer et al. teach aluminum trichloride as a useful catalyst in their process when used with a hydrosilane promoter. Ritzer et al. further teach that the resulting halogen-rich polysilanes can, in a separate step, be cleaved to form monosilanes.

Bokerman et al., U.S. Pat. No. 5,175,329, describe a process for the production of organosilanes from the high-boiling residue resulting from the direct process that results in a net consumption of organotrichlorosilane. In the described process the high-boiling residue is contacted with an organotrichlorosilane and hydrogen gas in the presence of both a hydrogenation catalyst and a redistribution catalyst.

Ferguson et al., U.S. Pat. No. 5,430,168, teach a process comprising forming a mixture comprising an organotrihalosilane and a high-boiling residue in the presence of hydrogen gas and a catalytic amount of aluminum trichtoride. The process results in a net consumption of the organotrihalosilane and the formation of monosilanes.

Barry et al., U.S. Pat. No. 2,681,355, teach that a high-boiling residue resulting from the direct process can be contacted with hydrogen chloride at elevated temperatures to form methylchlorosilanes.

Bluestein, U.S. Pat. No. 2,709,176, teaches heating an organohalogenpolysilane containing a silicon-silicon linkage at an elevated temperature in the presence of a tertiary organic amine and hydrogen halide to effect cleavage of the silicon-silicon bond and form organohatogenmonosilanes.

Chadwick et al., U.S. Pat. No. 5,292,912, teach a process comprising contacting a high-boiling residue from the direct process with hydrogen chloride at a temperature within a range of about 250° C. to 1000° C. in the presence of a catalyst selected from a group consisting of activated carbon, platinum supported on alumina, zeolite, aluminum trichloride, and aluminum trichloride supported on a support selected from a group consisting of carbon, alumina, and silica.

An object of the present invention is to provide a process where the high-boiling residue from a direct process for producing organohalosilanes can be converted into commercially useful monosilanes. An advantage of the process is that it may be run as a one-step process with no need to isolate more chlorinated intermediates, such as chlorodisilanes, and further treat to produce monosilanes. Another advantage of the process is that it can convert both disilanes and other silicon containing species comprising the high-boiling residue, such as slimethylenes and silalkylenes, to monosilanes.

SUMMARY OF INVENTION

The present invention is a hydrochlorination process for the production of monosilanes from the high-boiling residue resulting from the reaction of organochlorides with silicon metalloid in a process typically referred to as the "direct process." The process comprises forming a mixture comprising the high-boiling residue and an organosilane and contacting the mixture with hydrogen chloride in the presence of a catalytic amount of a catalyst composition effective in promoting the formation of monosilanes from the high-boiling residue. A preferred catalyst composition comprises aluminum trichloride, at least a portion of which may be formed in situ during conduct of the direct process and isolation of the high-boiling residue.

DESCRIPTION OF INVENTION

The present invention is a hydrochlorination process for converting a high-boiling residue resulting from the reaction of an organochloride with silicon metalloid to monosilanes. The process comprises: (A) forming a mixture comprising a high-boiling residue resulting from the reaction of an organochloride with silicon metalloid and an organosilane described by formula $$R_mH_nSiCl_{4-m-n},\qquad(1)$$

where each R is independently selected from a group consisting of alkyls comprising one to six carbon atoms, aryls, alkoxys comprising one to six carbon atoms, trimethylsilyl, and trifluoropropyl, m=1 to 4, n=0 to 2, and m+n=2 to 4; and (B) contacting the mixture with hydrogen chloride in the presence of a catalytic amount of a catalyst composition effective in promoting the formation of monosilanes from the high-boiling residue at a temperature within a range of about 150° C. to 500° C. and a total reactor pressure within a range of about 100 psig to 5,000 psig.

The present process can further comprise: recovering monosilanes described by formula

$$R_y H_z SiCl_{4-y-z},\qquad(2)$$

where R is described above, y=0 to 4, z=0 to 3, and y+z=0 to 4.

The present process may be run in any standard pressurizable reactor suitable for contact with chlorosilanes. The process may be run as a batch process or as a continuous process. The process may be run, for example, in a stirred-bed reactor, continuous stirred-tank reactor, a bubble-column reactor, a trickle-bed reactor, or a plug-flow reactor. In a preferred embodiment of the present invention, the present process is run as a one-step process with no additional processing steps being required to form the monosilanes from the high-boiling residue.

The present process is useful for converting a high-boiling residue resulting from the reaction of an organochloride with silicon metalloid to useful monosilanes. In a typical process for reacting an organochloride with silicon metalloid, the process is conducted at a temperature of about 300° C. to 350° C. in the presence of suitable catalysts and gaseous product and feed along with fine particulates are continuously removed from the process. The removed materials are subsequently distilled to recover organochlorosilanes, leaving a "high-boiling residue."

A preferred high-boiling residue for use in the present process is one with a boiling point above about 70° C. resulting from the distillation of organochlorosilanes from the reaction product of methyl chloride with silicon metalloid. A typical composition for such a high-boiling residue comprises: 50–60 wt % of disilanes of formula $Si_2Q_6$, where each Q is independently selected from a group consisting of methyl and chlorine and the disilane contains two to four methyl substituents per molecule; 15 to 25 weight percent silmethylenes described by formula $Q_3SiCH_2SiQ_3$, where Q is as previously described and the slimethylene contains two to four methyl substituents per molecule; silatkylenes described by formula $Q_3Si(SiQ_2)_a(CH_2)_b(SiQ_2)_cSiQ_3$, where Q is as previously described, a=0 to 4, b=1 to 3, c=0 to 4, and a+b+c≦2; 5 to 15 weight percent other high-boiling silicon-containing compounds; catalysts carried over from the direct process such as copper and compounds of copper; particulates containing silicon; and low levels of metals such as aluminum, calcium, and iron and compounds thereof.

In the present process a mixture of the high-boiling residue as described above is formed with an organosilane as described by formula (1). The mixture can be formed external to the reactor and added to the reactor or may be formed by adding the individual components to the reactor. The organosilane contains one to four substituents R, where each R is independently selected from a group consisting of alkyls comprising one to six carbon atoms, aryls, alkoxys comprising one to six carbon atoms, trimethylsilyl, and trifluoropropyl. Substituent R can be, for example, methyl, ethyl, propyl, isopropyl, tert-butyl, methoxy, ethoxy, phenyl, tolyl, naphthyl, trimethylsilyl, and trifluoropropyl. Preferred is when R is methyl.

The organosilane can be, for example, dimethyldichlorosilane, ethylmethyldichlorosilane, methylphenyldichlorosilane, 3,3,3-trifluoropropyl(methyl) dichtorosilane, methyldichlorosilane, ethyldichlorosilane, phenyldichlorosilane, trimethylchlorosilane, ethyldimethylchlorosilane, tetramethylsilane, trimethoxysilane, and mixtures of such organosilanes. Preferred is where the organosilane is selected from a group consisting of dimethyldichlorosilane, methyldichlorosilane, trimethylchlorosilane, and tetramethylsilane.

The weight percent of organosilane in the mixture with the high-boiling residue is not critical to the present process. Generally, a mixture where the organosilane is about 0.1 to 95 weight percent of the mixture is considered useful. Preferred is where the organosilane comprises about 30 to 50 weight percent of the mixture.

The mixture is contacted with hydrogen chloride, which may be fed to the reactor as a gas. The concentration of hydrogen chloride fed to the reactor is not critical and can be any amount sufficient to effect a desirable level of hydrochlorination. Preferred is when the amount of hydrogen chloride fed to the reactor is within a range of about 1 to 70 weight percent, based on the weight of the high-boiling residue fed to the reactor. Even more preferred is when the amount of hydrogen chloride fed to the reactor is within a range of about 15 to 50 weight percent, on the same basis.

The contacting of the present process is effected in a reactor under a pressure of about 100 psig to 5,000 psig ensuring that at least a portion of the hydrogen chloride is in a liquid phase. More preferred is when the contacting is effected in a reactor under a pressure of about 300 psig to 1,500 psig. Most preferred is when the contacted is effected in a reactor under a pressure of about 600 psig to 1,100 psig.

The mixture comprising the high-boiling residue and organosilane is contacted with the hydrogen chloride in the presence of a catalytic amount of a catalyst composition effective in promoting formation of monosilane from the high-boiling residue. The catalyst composition required in the present process promotes the formation of monosilanes from the high-boiling residue. The present inventors believe that the process requires a catalytic composition which promotes redistribution of alkyl and chlorine groups between silicon atoms, hydrochlorination, and scission of silicon-silicon bonds and optionally silicon-carbon bonds. Therefore, the catalyst composition can comprise one or more chemical entities providing the described activities to the catalyst composition.

Generally, any Lewis Acid or its equivalent may be used to provide redistribution activity to the catalyst composition. Examples of chemical entities useful to effect redistribution in the present process include those described in Ritzer et al., U.S. Pat. No. 4,393,229, and in Bokerman et al., U.S. Pat. No. 5,175,329, which are hereby incorporation by reference for their teaching of such redistribution catalyst. Examples of such chemical entities useful to effect redistribution in the present process include aluminum trichloride, antimony pentachloride, zirconium tetrachloride, potassium aluminum tetrachloride, quaternary phosphonium halides, quaternary ammonium halides, ammonium halides, cuprous chloride, boric acid, and boron halides.

Examples of chemical entities useful in the present catalyst composition to effect hydrochlorination include aluminum trichloride, antimony pentachloride, cuprous chloride, copper metal, copper salts, complexes of copper salts with organic ligands, and those hydrogenation catalysts described in Bokerman et al., U.S. Pat. No. 5,175,329, which is hereby incorporated by reference for such teachings.

Generally those chemical entities which promote redistribution of alkyl and chlorine groups between silicon atoms and those chemical entities which promote hydrochlorination in the present process also promote scission of silicon-silicon bonds and optionally silicon-carbon bonds. Therefore, it is generally not necessary to add additional chemical entities to the catalyst composition to promote the scission of the silicon-silicon bonds and optionally silicon-carbon bonds. If such chemical entities are needed a chemical entity such as aluminum trichloride or antimony pentachloride may be added to the composition.

In the present process it is preferred that the catalyst composition comprise a single chemical entity which promotes redistribution, hydrochlorination, and bond scission under process conditions. Such single chemical entities include aluminum trichloride and antimony pentachloride.

The present process requires the presence of a "catalytic amount" of a catalyst composition as described above. By "catalytic amount" it is meant an amount of the catalyst composition sufficient to facilitate the conversion of silicon containing compounds in the high-boiling residue to monosilanes. A preferred catalytic amount of catalyst composition is that sufficient to facilitate the conversion of polysilanes, for example methylchlorodisilanes, silmethylenes, and silalkylenes in the high-boiling residue to monosilanes. The amount of catalyst composition required will depend upon the chemical entities comprising the catalyst composition, and such amounts can be easily determined by those skilled in the art.

When aluminum trichloride or antimony pentachloride comprise the catalyst composition, about 0.01 to 20 weight percent of catalyst composition based on the combined weight of the catalyst composition and the high-boiling residue is considered useful in the present process. Preferred is when the aluminum trichloride or antimony pentachloride concentration is within a range of about 0.5 to 5 weight percent, on the same basis.

A preferred catalyst composition for use in the present process is aluminum trichloride. The aluminum trichloride may be added to the process as the compound or may be formed in situ by the addition of materials that form aluminum trichloride. All or a portion of the catalytic amount of aluminum trichloride may be formed in situ during conduct of the direct process and isolation of the monosilane fraction to form the high-boiling residue. The source of the aluminum and chlorine necessary to form the aluminum trichloride can be the raw materials used in the direct process, particularly the silicon metalloid and organochloride feed. The catalytic amount of aluminum trichloride can be a combination of added aluminum trichloride and that in situ formed aluminum trichloride remaining in the high-boiling residue as isolated from the direct process.

The present process can be conducted at a temperature within a range of about 150° C. to 500° C. Preferred is a temperature within a range of about 275° C. to 425° C. Most preferred is a temperature within a range of about 300° C. to 375° C.

Monosilanes as described by formula (2) can be recovered from the present process. The monosilanes can be separated by standard methods for separating liquid mixtures, for example, distillation. The monosilanes can contain zero to four substituents R, where R is as previously described. The monosilane can contain zero to three hydrogens substituted on each silicon atom. The monosilanes can contain zero to four chlorine atoms substituted on each silicon atom.

The following example is provided to illustrate the present invention. The example is not intended to limit the claims herein. In the example, Me represents a methyl radical.

Example. The ability of aluminum trichloride to catalyze the conversion of a mixture comprising a high-boiling residue and a mixture comprising methyldichlorosilane and trimethylchlorosilane in the presence of hydrogen chloride was evaluated in a stirred-batch reactor. The reactor was a 650 ml, pneumatically stirred, Parr Bomb reactor. A mixture comprising 28.7 weight percent of a filtered high-boiling residue from a direct process for the preparation of methylchlorosilanes by the reaction of methyl chloride with silicon metalloid, about 68.2 weight percent trimethylchlorosilane, and 3.1 weight percent methyldichlorosilane was added to the reactor. The major components of the high-boiling residue are presented in Table 1 on a weight percent basis.

TABLE 1

| Major Components of High-Boiling Residue | |
|---|---|
| Component | Weight Percent |
| $Cl_2MeSiSiMe_2Cl$ | 27.2 |
| $Cl_2MeSiSiMeCl_2$ | 52.9 |
| $Cl_2MeSiCH_2SiMe_2Cl$ | 7.9 |
| $Cl_2MeSiCH_2SiMeCl_2$ | 12.0 |

About 3.5 weight percent of aluminum trichloride was present in the reactor, based on the weight of the high-boiling residue. About 0.3 to 0.4 mole of hydrogen chloride gas was fed to the reactor. The reactor was heated to about 325° C. and stirred for about 3 hours, with an internal reactor pressure of approximately 700 psig to 1000 psig.

At the end of the run a sample from the reactor was analyzed by gas chromatography using a thermal conductivity detector. The results of this analysis are reported in Table 2. The conversion of the high-boiling residue to monosilanes was 81.2 weight percent. The product distribution is presented in Table 2 as a net value calculated as the weight percent species of monosilane represents of the total monosilane present in the product.

TABLE 2

| Monosilane Product Distribution | |
|---|---|
| Monosilane | Weight Percent |
| $Me_2HSiCl$ | 0.8 |
| $MeHSiCl_2$ | 5.0 |
| $MeSiCl_3$ | 23.9 |
| $Me_2SiCl_2$ | 70.3 |

We claim:

1. A process for converting a high-boiling residue resulting from the reaction of an organochloride with silicon metalloid to monosilanes, the process comprising:

(A) forming a mixture comprising a high-boiling residue resulting from the reaction of an organochloride with silicon metalloid and an organosilane described by formula

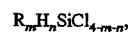

where each R is independently selected from a group consisting of alkyls comprising one to six carbon atoms, aryls, alkoxys comprising one to six carbon atoms, trimethylsilyl, and trifluoropropyl, m=1 to 4, n=0 to 2, and m+n=2 to 4; and (B) contacting the mixture with hydrogen chloride in the presence of a catalytic amount of a catalyst composition effective in promoting the formation of monosilanes from the high-boiling residue at a temperature within a range of about 150° C. to 500° C. and a total reactor pressure within a range of about 100 psig to 5,000 psig.

2. A process according to claim 1, where the high-boiling residue has a boiling point above about 70° C. and results from the distillation of methylchlorosilanes from the reaction product of methyl chloride with silicon metalloid.

3. A process according to claim 1, where the organosilane is trimethylchlorosilane.

4. A process according to claim 1, where the organosilane comprises about 0.1 to 95 weight percent of the mixture.

5. A process according to claim 1, where the organosilane comprises about 30 to 50 weight percent of the mixture.

6. A process according to claim 1, where the amount of hydrogen chloride contacted with the mixture is within a range of about 1 to 70 weight percent, based on the weight of the high-boiling residue.

7. A process according to claim 1, where the amount of hydrogen chloride contacted with the mixture is within a range of about 15 to 50 weight percent, based on the weight of the high-boiling residue.

8. A process according to claim 1, where the reactor pressure is about 300 psig to 1,500 psig.

9. A process according to claim 1, where the catalyst composition is selected from a group consisting of aluminum trichloride and antimony pentachloride.

10. A process according to claim 9, where the catalyst composition comprises about 0.01 to 20 weight percent, based on the combined weight of the catalyst composition and the high-boiling residue.

11. A process according to claim 9, where the catalyst composition comprises about 0.5 to 5 weight percent, based on the combined weight of the catalyst composition and the high-boiling residue.

12. A process according to claim 1, where the catalyst composition consist essentially of aluminum trichloride.

13. A process according to claim 1, where the catalyst composition consist essentially of antimony pentachloride.

14. A process according to claim 12, where at least a portion of the aluminum trichloride is formed in situ.

15. A process according to claim 1, where the temperature is within a range of about 275° C. to 425° C.

16. A process according to claim 1, where the temperature is within a range of about 300° C. to 375° C.

17. A process according to claim 1 further comprising recovering monosilanes described by formula $$R_yH_zSiCl_{4-y-z}$$

where R is as previously described, y=0 to 4, z=0 to 3, and y+z=0 to 4.

18. A process according to claim 1, where the forming and contacting of the mixture is conducted as a one-step process thereby forming monosilanes.

19. A one-step process for converting a high-boiling residue resulting from the reaction of an organochloride with silicon metalloid to monosilanes, the process comprising:

(A) forming a mixture comprising a high-boiling residue resulting from the reaction of methyl chloride with silicon metalloid and trimethylchlorosilane, and (B) contacting the mixture with hydrogen chloride in the presence of about 0.5 to 5 weight percent aluminum chloride, based on the combined weight of the aluminum chloride and the high-boiling residue, at a temperature within a range of about 300° C. to 375° C. and a total reactor pressure within a range of about 600 psig to 1,100 psig and thereby forming monosilanes.

\* \* \* \* \*